United States Patent [19]

Wiedenmann et al.

[11] Patent Number: 5,169,512
[45] Date of Patent: Dec. 8, 1992

[54] PLANAR POLAROGRAPHIC PROBE FOR DETERMINING THE LAMBDA VALUE OF GAS MIXTURES

[75] Inventors: Hans-Martin Wiedenmann, Stuttgart; Gerhard Schneider, Schwieberdingen; Kurt Bayha, Oberriexingen, all of Fed. Rep. of Germany

[73] Assignee: Robert Bosch GmbH, Stuttgart, Fed. Rep. of Germany

[21] Appl. No.: 566,373
[22] PCT Filed: Mar. 21, 1989
[86] PCT No.: PCT/DE89/00174
   § 371 Date: Sep. 18, 1990
   § 102(e) Date: Sep. 18, 1990
[87] PCT Pub. No.: WO89/09933
   PCT Pub. Date: Oct. 19, 1989

[30] Foreign Application Priority Data
   Apr. 8, 1988 [DE] Fed. Rep. of Germany .... 3811713.4

[51] Int. Cl.⁵ .............................................. G01N 27/26
[52] U.S. Cl. .................................... 204/426; 204/424; 204/425; 204/427
[58] Field of Search ................ 204/426, 425, 424, 427

[56] References Cited

U.S. PATENT DOCUMENTS

| | | | |
|---|---|---|---|
| 4,305,803 | 12/1981 | Beyer et al. | 204/195 S |
| 4,312,736 | 1/1982 | Menth et al. | 204/290 R |
| 4,334,510 | 6/1982 | Croset et al. | 123/440 |
| 4,579,643 | 4/1986 | Mase et al. | 204/426 |
| 4,645,572 | 2/1987 | Nishizawa et al. | 204/1 T |
| 4,647,364 | 3/1987 | Mase et al. | 204/426 |

FOREIGN PATENT DOCUMENTS

| | | |
|---|---|---|
| 0193379 | 9/1986 | European Pat. Off. . |
| 0203351 | 12/1986 | European Pat. Off. . |
| 0259175 | 3/1988 | European Pat. Off. . |
| 3728618 | 3/1988 | Fed. Rep. of Germany . |

*Primary Examiner*—John Niebling
*Assistant Examiner*—Bruce F. Bell
*Attorney, Agent, or Firm*—Frishauf, Holtz, Goodman & Woodward

[57] ABSTRACT

A planar polarographic probe for determining the λ value of gas mixtures, in particular of exhaust gases of internal combustion engines, having at least the following units: a pumping cell (A), a diffusion unit (B) with a diffusion resistance preceding a pumping electrode of the pumping cell (A) and, if necessary, a heating unit (C) is proposed in which the diffusion resistance of the diffusion unit (B) is formed by a preshaped body which becomes porous on sintering and which is inserted into the unsintered probe.

Such a polarographic probe enables a sensor to be constructed in a simple manner which is particularly suitable for production, with increased reproducibility of the diffusion resistance.

11 Claims, 8 Drawing Sheets

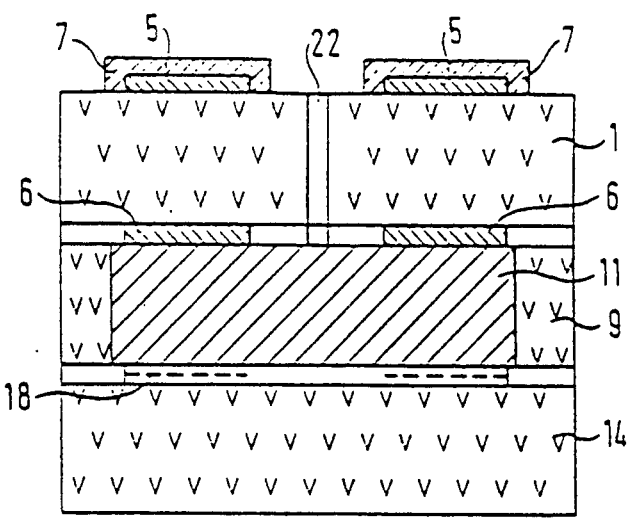
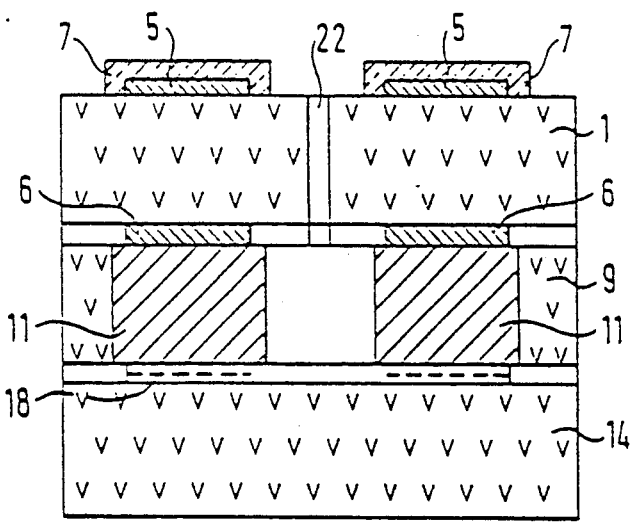
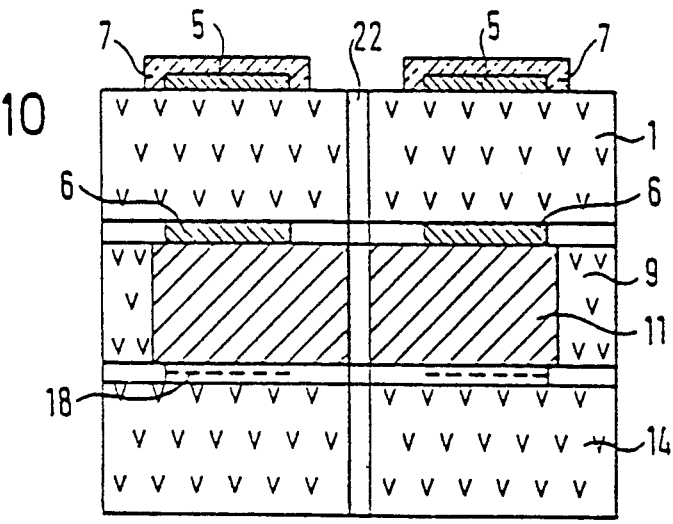

Fig. 11
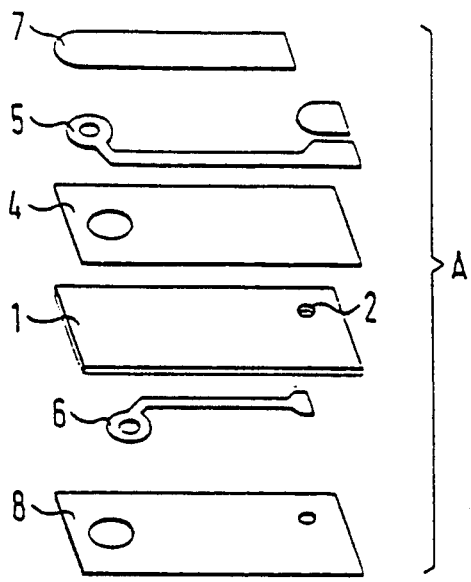
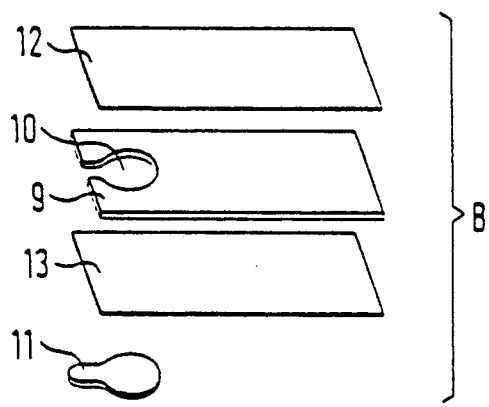
Fig. 12
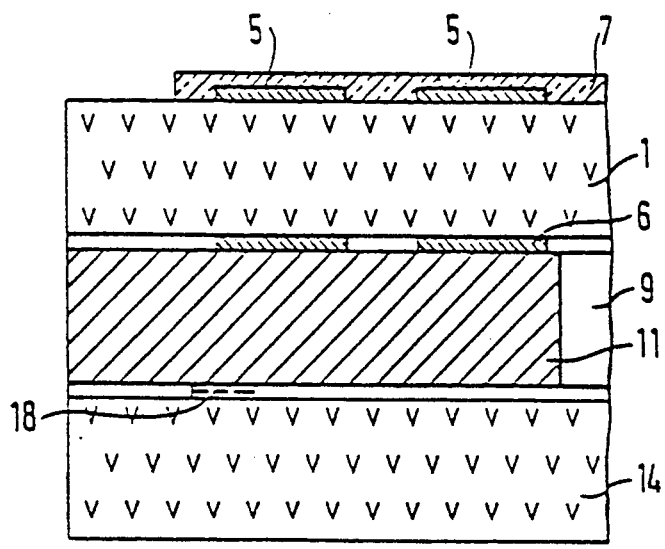

Fig. 13
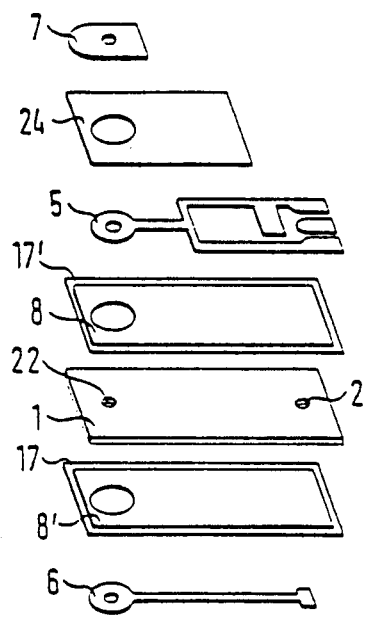
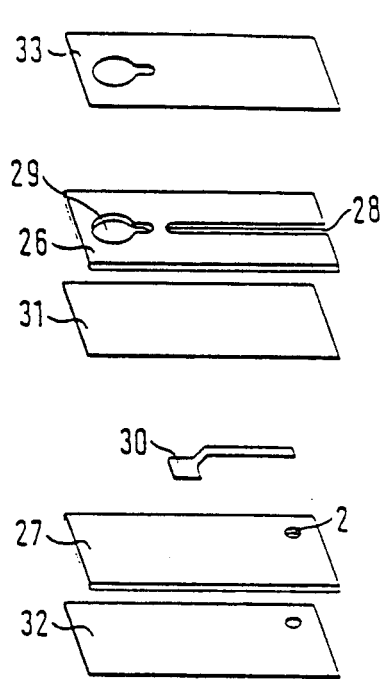
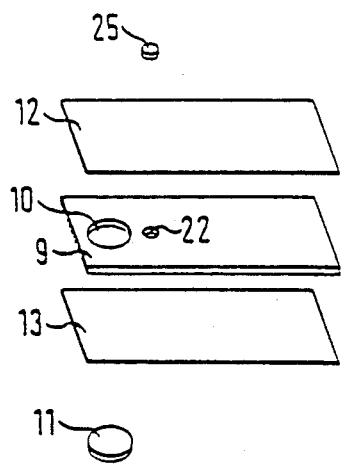
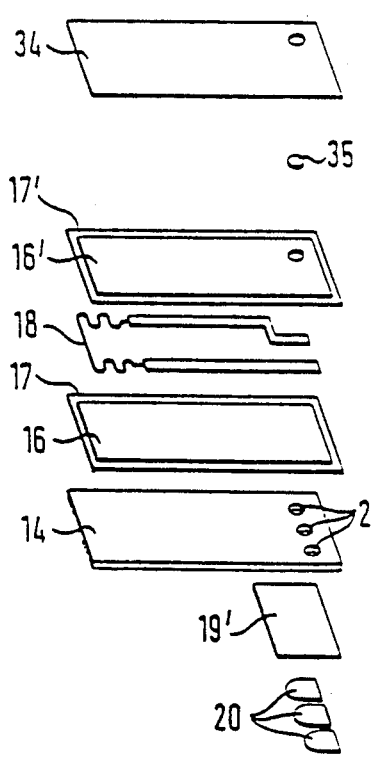

PLANAR POLAROGRAPHIC PROBE FOR DETERMINING THE LAMBDA VALUE OF GAS MIXTURES

PRIOR ART

The invention is based on a planar polarographic probe of the generic type of the main claim. In such polarographic probes, which operate in accordance with the diffusion resistance principle, the diffusion current at a constant voltage present at the two electrodes of the probe, or the diffusion limit current is measured. In an exhaust gas produced during combustion processes, this current is dependent on the oxygen concentration for as long as the diffusion of the gas to the pumping electrode determines the velocity of the reaction occurring. It is known to construct such polarographic probes operating in accordance with the polarographic measuring principle, in such a manner that both anode and cathode are exposed to the gas to be measured, the cathode exhibiting a diffusion barrier.

As a rule, the known polarographic probes are used for determining the λ value of gas mixtures which designates the ratio between "total oxygen/oxygen needed for the complete combustion of the fuel" of the fuel/air mixture burning in a cylinder, the probes determining the oxygen content of the exhaust gas via an electrochemical change in potential.

Due to a simplified and inexpensive method of production, the production of probes and sensor elements which can be produced in ceramic foil and screen printing technique has become successful in practice in recent years.

Starting with platelet or foil-shaped oxygen-conducting solid electrolytes, for example of stabilized zirconium dioxide, planar polarographic probes can be produced in a simple and economical manner which are coated on both sides with an inner and outer pumping electrode each with the associated conductor tracks. In this arrangement, the inner pumping electrode is advantageously located in the edge region of a diffusion channel through which the gas to be measured is supplied and which serves as gas diffusion resistance.

Furthermore, sensor elements and detectors are known from German Offenlegungsschrift 3,543,759 and EP-A 0,142,992, 0,142,993, 0,188,900 and 0,194,082, which have in common that they exhibit in each case a pumping cell and a sensor cell which consist of platelet- or foil-shaped oxygen-conducting solid electrolytes and two electrodes arranged thereupon and exhibit a common diffusion channel.

A certain disadvantage of known polarographic probes and sensor elements consists in the fact that the front part of the inner pumping electrode, which faces the supplied gas to be measured, is utilized to a greater extent than the rear part of the pumping electrode which faces away from the supplied gas to be measured. This leads to a high electrode polarization which requires a high pumping voltage. The latter, in turn, entails the risk of electrolyte decomposition in the region of the inner pumping electrode.

It is therefore proposed in German Offenlegungsschrift 3,728,618 to arrange, in a sensor element for polarographic probes for determining the λ value of gas mixtures with an (sic) outer and inner pumping electrodes which are arranged on platelet- or foil-shaped solid electrolytes conducting $O^{2-}$-ions, of which the inner pumping electrode is arranged on the platelet- or foil-shaped solid electrolyte in a diffusion channel for the gas to be measured, and with conductor tracks for the pumping electrodes, at least a second inner pumping electrode which is short-circuited with the first inner pumping electrode on the side opposite to the inner pumping electrode in the diffusion channel.

It is furthermore disadvantageous in known planar polarographic probes that their method of production is frequently complicated and therefore expensive, that the diffusion resistance is uncontrollably affected in subsequent process steps and thus the reproducibility of the diffusion resistance is unsatisfactory and that furthermore its constancy under severe use in the exhaust gas of internal combustion engines is inadequate.

ADVANTAGES OF THE INVENTION

By comparison, the polarographic probe according to the invention, having the characterizing features of the main claim, has the advantage that it makes possible a simple construction of a sensor which is thus suitable for production, that the diffusion range of the probe is largely insensitive to change in the subsequent process steps, for example cracking or deformation due to lamination, stamping, cutting, sintering etc., in contrast to screen-printed diffusion systems, that an increased reproducibility of the diffusion resistance is achieved, that it is possible to influence the sensor characteristic in a direct and defined way via the design of the porous-sintering preshaped bodies, that the arrangement of the gas supply opening is variable independently of the diffusion resistance, that the electrode design is variable within wide limits and that, finally, the possibility is given for expanding the design to a wide band sensor.

The planar polarographic probe according to the invention can be used instead of known probes of planar structure. The probe according to the invention can thus be used as lean-mixture sensor for diesel engines and as such installed in a conventional sensor housing, for example of the type known from German Offenlegungsschriften 3,206,903 and 3,537,051 and used for measuring the fuel/air ratio in a lean exhaust gas.

However, the polarographic probe according to the invention can also additionally exhibit, in addition to the pumping cell, a Nernst cell (concentration cell) which is provided with an additional air reference channel and the one electrode of which is arranged in the area of the pumping electrode in the diffusion channel of the pumping cell and the other electrode of which is located in the air reference channel.

According to a preferred embodiment, a planar polarographic probe according to the invention can be simply and advantageously produced by laminating together and sintering a pumping cell (A) of a first solid electrolyte foil with at least one outer pumping electrode and at least one inner pumping electrode with a diffusion unit (B) of a second solid electrolyte foil and a third solid electrolyte foil which, if necessary, has been constructed to form a heater unit (C).

According to the invention, a solid electrolyte foil is used as diffusion unit (B) in this connection, having an opening forming a diffusion zone into which a preshaped body becoming porous on sintering at sintering temperature is inserted. As diffusion unit (B), a solid electrolyte foil is advantageously used from which an opening forming the diffusion zone has been stamped out into which a foil section stamped out of a foil which becomes porous on sintering is inserted.

In this connection, it has been found to be particularly advantageous to use as foil insert which becomes porous on sintering an insert of ceramic material having a thermal expansion behaviour which corresponds to or at least approaches the expansion behaviour of the solid electrolyte foils used. A foil insert of the ceramic material of which the solid electrolyte foils building up the probe also consist is advantageously used, in which connection the porosity of the insert can be created by adding pore formers which burn, decompose or evaporate during the sintering process. Typical pore formers which can be used are, for example, thermal soot powders, plastics, for example based on polyurethane, salts, for example, ammonium carbonate and organic substances such as, for example, theobromine and indanthrene blue.

Such pore forming agents are added to the material which becomes porous on sintering, for example the starting material used for producing a foil which becomes porous on sintering, in such a quantity that a material having a porosity of 10 to 50% is produced. The mean pore diameter, which can be determined by the particle size of the pore forming agent used, is preferably about 5 to 50 $\mu$m.

Furthermore, it has been found to be advantageous if an insert is used which becomes porous on sintering the diameter of which is slightly smaller and the thickness of which is slightly greater than the thickness of the foil used for producing the diffusion unit. This ensures reliable insertion of the bodies which becomes porous on sintering into the prepared opening in the foil of the diffusion unit and the formation of a good bond between pumping cell (A), diffusion unit (B) and heater unit (C) in the sintered state.

Furthermore, it has been found to be advantageous if the outer diameter of the electrode layout is kept slightly smaller than the diameter of the diffusion zone. This ensures that the inner pumping electrode is within the porous diffusion barrier. It has also been found to be suitable if the diameter of the diffusion zone does not exceed 75% of the width of the polarographic probe.

The gas to be measured can be supplied via a diffusion hole in the pumping cell (A), a diffusion hole in the heater unit (C) or else via the diffusion unit (B). In the latter case, the polarographic probe does not contain a diffusion hole. In this case, the diffusion processes occur directly via the diffusion insert which becomes porous on sintering and which is laterally cut.

The body, which becomes porous on sintering during the sintering process of the polarographic probe, can take up the entire space of the recess in the foil of the diffusion unit (B) or also only a part thereof as will be shown in the examples of advantageous embodiments of probes according to the invention following later. Thus, it is possible, for example to coat the preshaped body, which becomes porous on sintering during the sintering process of the polarographic probe, for example before it is stamped out of a foil which becomes porous on sintering, with a substance which is combustible, vaporizable or decomposable in the presintering range, such as, for example, theobromine or indanthrene blue, for example in the screen printing process. If such a preshaped body is used, a gap is produced between the inner pumping electrode and the insert during the sintering process, which prevents a partial covering of the pumping electrode by the preshaped body which becomes porous on sintering.

The preshaped body, which becomes porous on sintering during the sintering process of the polarographic probe, can exhibit a central hole if necessary. Use of such a preshaped body can be particularly advantageous when the gas to be measured is supplied into the diffusion zone via a diffusion hole in the heater unit (C) and/or pumping cell (A). In these cases, there is no porous diffusion insert at the end of the diffusion hole. This additionally prevents a contamination of the preshaped body, which becomes porous on sintering, at the bottom of the diffusion hole.

The pumping cell (A) and the heater unit (C) have a structure which is known for planar polarographic probes.

Thus, the pumping cell (A) essentially consists of a solid electrolyte foil with an outer pumping electrode and an inner pumping electrode and the associated conductor tracks and through-contacts. Electrodes and conductor tracks in this arrangement are insulated from the solid electrolyte foil by an insulation based on, for example, $Al_2O_3$. The outer pumping electrode is covered with a porous protection layer (Engobe). The pumping cell (A) is laminated to the diffusion unit (B) by means of an interlaminar binder of conventional known composition.

The heater unit (C) essentially consists of a further solid electrolyte foil with stamped-out through-contact holes, a layer which insulates the heater from the solid electrolyte foil, the actual heater, an insulation layer over the heater, heater connections and an insulation for the heater connections. Further details of the structure of pumping cell (A) and heater unit (C) are obtained from the description of preferred embodiments of polarographic probes according to the invention, following later.

A polarographic probe according to the invention is produced by laminating together pumping cell (A), diffusion unit (B) and heater unit (C) and, if necessary, further units such as, for example, a Nernst cell, in that the pumping cell (A) and the units (B) and (C) are joined together under pressure and subsequently sintered at sintering temperatures in the range from 1300 to 1550° C.

If the polarographic probe according to the invention additionally exhibits a Nernst cell (N) in accordance with a further advantageous development, its one electrode is advantageously arranged in the area of the pumping electrode behind the preshaped bodies, which becomes porous on sintering, forming the diffusion resistance, and thus exposed to the exhaust gas whilst the other electrode of the Nernst cell is connected to a conventional metal/metal oxide reference body or a reference gas, preferably to air, in a reference channel.

Thus, a polarographic probe according to the invention which is constructed as wideband sensor advantageously consists of at least the following units:
  the pumping cell (A),
  the diffusion unit (B),
  the Nernst cell (N) of two solid electrolyte foils, one foil containing the exhaust gas electrode and the reference channel and the other foil containing the reference electrode, and
  the heater unit (C), in which arrangement the diffusion unit (B) exhibits a through-contact to the Nernst exhaust gas electrode and the heater unit (C) exhibits a through-contact to the Nernst reference electrode.

Known solid electrolyte foils conducting $O^{2-}$ ions, based on oxides of quadrivalent metals such as, in particular, $ZrO_2$, $CeO_2$, $HfO_2$ and $ThO_2$ with a content of bivalent alkaline earth metal oxides and/or preferably trivalent oxides of the rare earths are suitable for producing the polarographic probes according to the invention. The foils can typically consist of approximately 50 to 97 mol% of $ZrO_2$, $CeO_2$, $HfO_2$ or $ThO_2$ and 50 to 3 mol% of CaO, MgO or SrO and/or oxides of the rare earths and, in particular, $Y_3O_3$. The solid electrolyte foils advantageously consist of $ZrO_2$ stabilized with $Y_2O_3$. The thickness of the foils used is advantageously about 0.1 to 0.6 mm.

The pumping electrodes and the associated conductor tracks can be printed in the usual known manner, starting with pastes based on noble metal, particularly based on platinum or based on noble metal/cermet, particularly based on platinum/cermet, on the solid electrolyte foils which are advantageously partially provided with an insulating layer. The layout of the pumping electrodes is adapted to the embodiment of the diffusion unit.

The heater can be correspondingly printed on a previously insulated solid electrolyte foil during the production of the heater unit (C). A corresponding heater layout enables diffusion holes to be stamped or drilled without damaging the heater conductor track. The heater can be sealed by means of frames printed onto the foil as will still be shown later in detail.

BRIEF DESCRIPTION OF DRAWINGS

The drawing shows particularly advantageous embodiments of polarographic probes according to the invention by way of example The probes shown have in common that they are constructed of at least three foil units, namely
 the pumping cell (A);
 the diffusion unit (B) and
 the heater unit (C) and, if necessary,
 a Nernst cell (N).
In detail:

FIG. 8 shows a cross-section through the diffusion zone of a planar polarographic probe according to FIG. 7;

FIG. 9 shows a cross-section through the diffusion zone of a fifth embodiment of a planar polarographic probe according to the invention;

FIG. 10 shows a cross-section through the diffusion zone of a sixth embodiment of a planar polarographic probe according to the invention;

FIG. 11 shows the layout of units (A) and (B) of a seventh embodiment of a planar polarographic probe according to the invention;

FIG. 12 shows a longitudinal section through the diffusion zone of a planar polarographic probe according to FIG. 12 (sic);

FIG. 13 shows the layout of an eighth embodiment of a planar polarographic probe according to the invention which, in addition to a pumping cell (A), a diffusion unit (B) and a heater unit (C), exhibits a Nernst cell (N) and thus represents a wideband sensor;

DESCRIPTION OF THE PREFERRED EMBODIMENT

Figure 1:
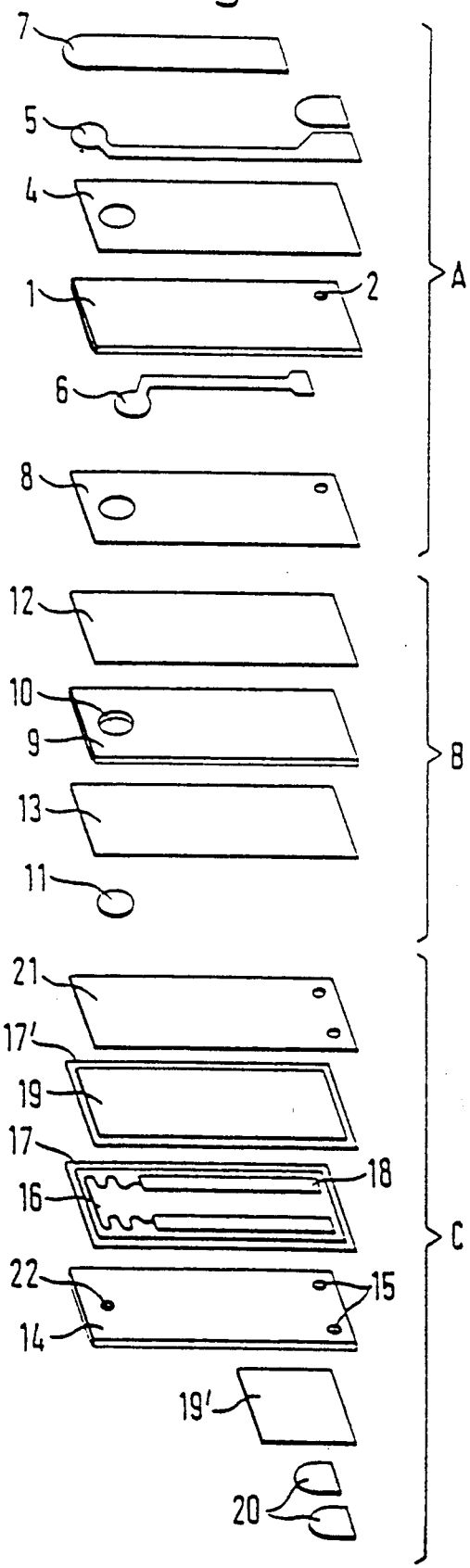
FIG. 1 shows the layout of a first embodiment of a planar polarographic probe according to the invention.
Figure 2:
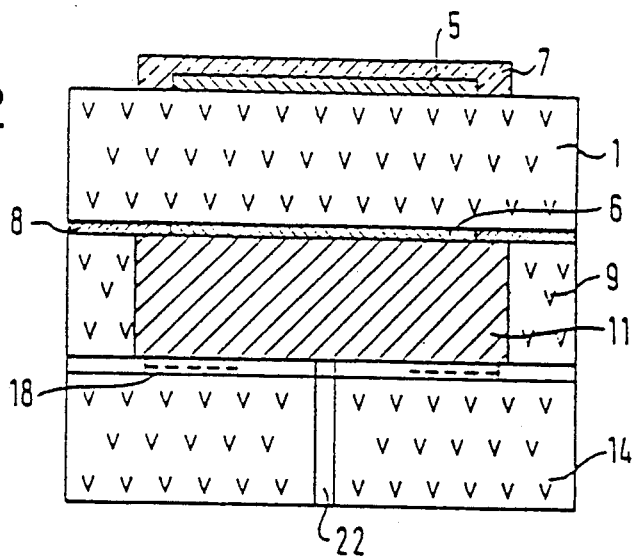
FIG. 2 shows a cross-section through the diffusion zone of a polarographic probe according to FIG. 1.

According to the first embodiment shown diagrammatically in FIGS. 1 and 2, the pumping cell (A) is constructed of the solid electrolyte foil 1 with stamped-out through-contact hole 2; the insulation 4, the outer pumping electrode 5, the inner pumping electrode 6 and the protective layer (Engobe) 7. A layer of an interlaminar binder 8 is used for the connection with the diffusion unit (B). As shown, the electrodes in each case exhibit a conductor track and connections.

The diffusion unit (B) consists of the solid electrolyte foil 9 with stamped-out diffusion zone 10, the preshaped bodies 11 and the layers 12 and 13 of interlaminar binder.

The heater unit (C) consists of the solid electrolyte foil 14 with stamped-out contact holes 15 and stamped-out diffusion hole 22, the heater insulation 16, the frame 17 and 17', the heater 18, the heater insulation 19 and 19' and the heater connections 20. The heater unit (C) is laminated together with the diffusion unit (B) via the layer 21 of interlaminar binder.

Figure 3:
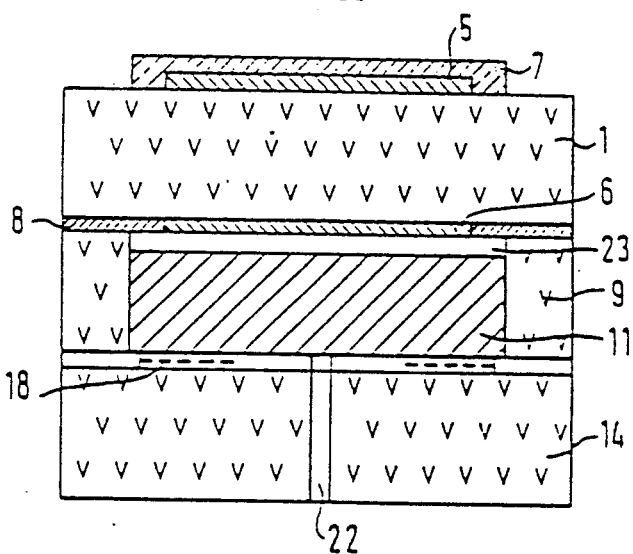
FIG. 3 shows a cross-section through the diffusion zone of a polarographic probe according to FIG. 1 with air gap between inner pumping electrode and porous foil insert.

The embodiment of a further polarographic probe according to the invention, shown in cross-section in FIG. 3, only differs from the embodiment according to FIGS. 1 and 2 in that a preshaped body which becomes porous on sintering was used for its production, which body was stamped out of a foil which becomes porous on sintering and which was first coated with a substance which is combustible, decomposable or vaporizable in the presintering range, for example theobromine or indanthrene blue. As a result, the probe contains a gap 23 between the inner pump electrode 6 and the porous preshaped bodies 11, the structure being otherwise identical.

Figure 4:
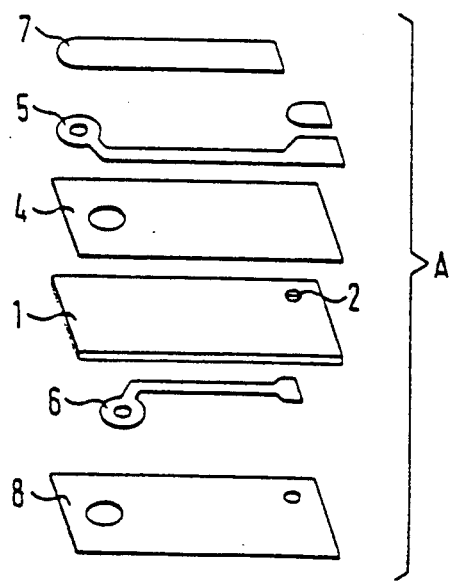
FIG. 4 shows the layout of the pumping cell (A) of a second embodiment of a planar polarographic probe according to the invention.
Figure 5:
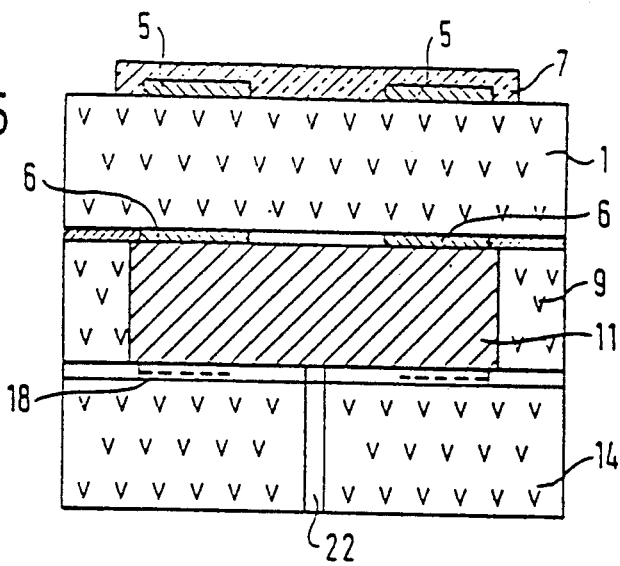
FIG. 5 shows a cross-section through the diffusion zone of a planar polarographic probe according to FIG. 4.

The second embodiment shown diagrammatically in FIGS. 4 and 5 only differs from the first embodiment in the electrode layout There can also be a gap 23 between the inner pumping electrode 6 and the porous diffusion insert 11 in the case of this second embodiment.

Figure 6:
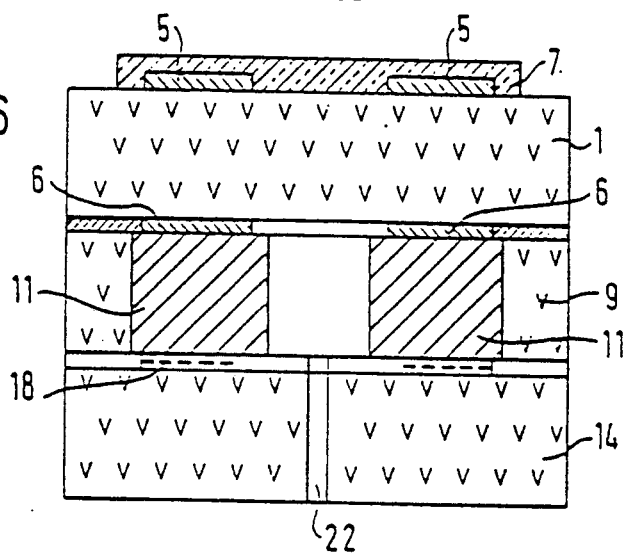
FIG. 6 shows a cross-section through the diffusion zone of a third embodiment of a planar polarographic probe according to the invention.

The third embodiment of a polarographic probe according to the invention, shown diagrammatically in FIG. 6, only differs from the embodiment according to FIGS. 4 and 5 in that it exhibits a preshaped body 11 which becomes porous on sintering and which has a centre hole so that there is no diffusion insert at the end of the diffusion hole 22.

Figure 7:
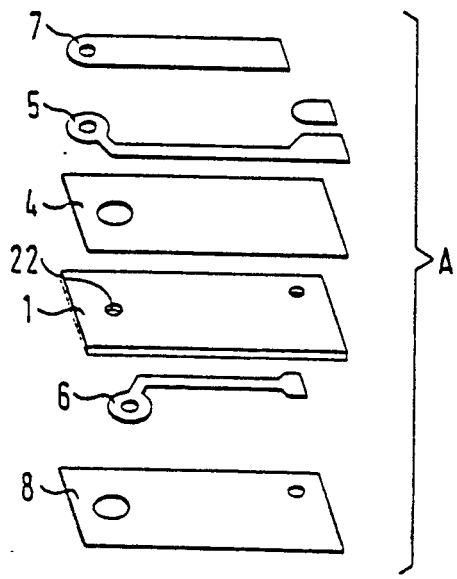
FIG. 7 shows the layout of the pumping cell (A) of a fourth embodiment of a planar polarographic probe according to the invention.

In the fourth embodiment of a probe according to the invention, shown diagrammatically in FIGS. 7 and 8, the diffusion hole 22 is not located in the heater unit (C) but in the pumping cell (A).

The fifth embodiment of a polarographic probe according to the invention, shown diagrammatically in FIG. 9, only differs from the fourth embodiment according to FIGS. 7 and 8 in that it contains as insert a preshaped body which becomes porous on sintering and has a centre hole.

In the sixth embodiment of a polarographic probe according to the invention, shown diagrammatically in FIG. 10, the diffusion hole 22 extends through the entire probe.

In the case of the seventh embodiment of a polarographic probe according to the invention, shown diagrammatically in FIGS. 11 and 12, the probe does not exhibit a diffusion hole. In this case, the diffusion zone 10 of the diffusion unit (B) extends past the sensor end. In a modified manner, the electrode layout can correspond, for example, also to the electrode layout of the embodiment shown in FIGS. 1 and 2.

Figure 14:
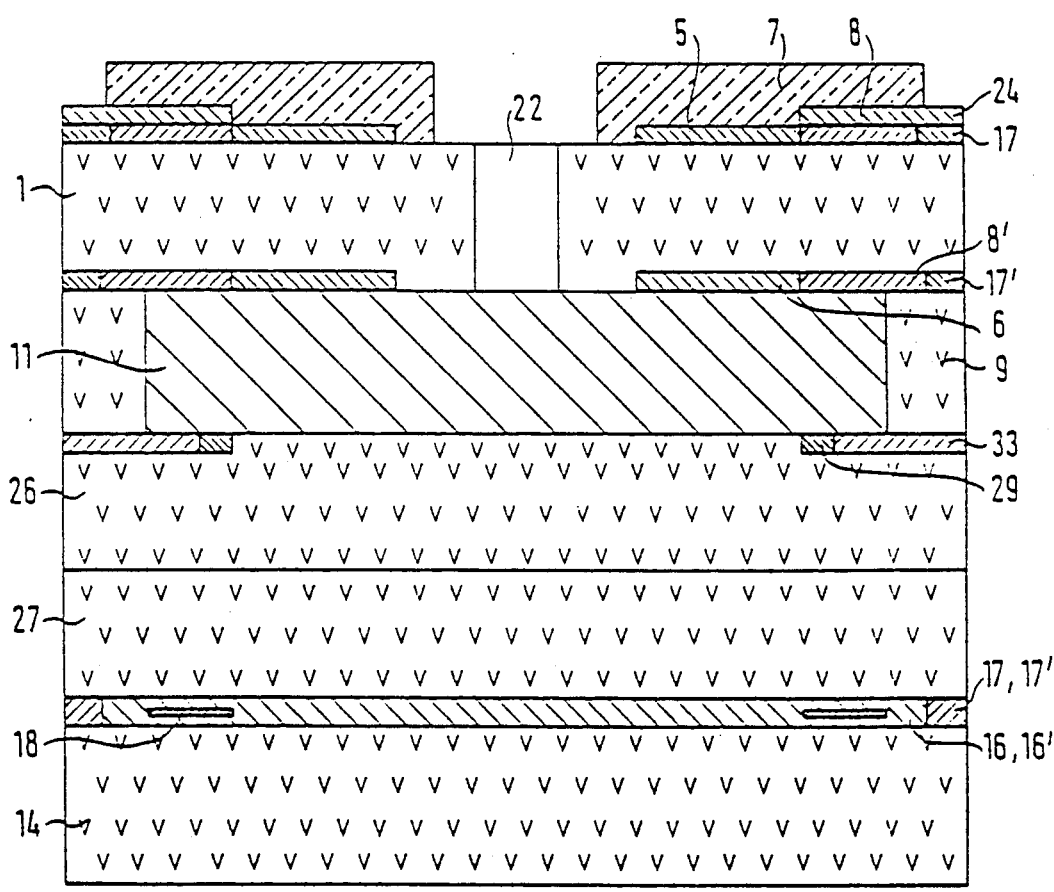
FIG. 14 shows a cross-section through the diffusion zone of a wideband sensor according to FIG. 13.
Figure 15:
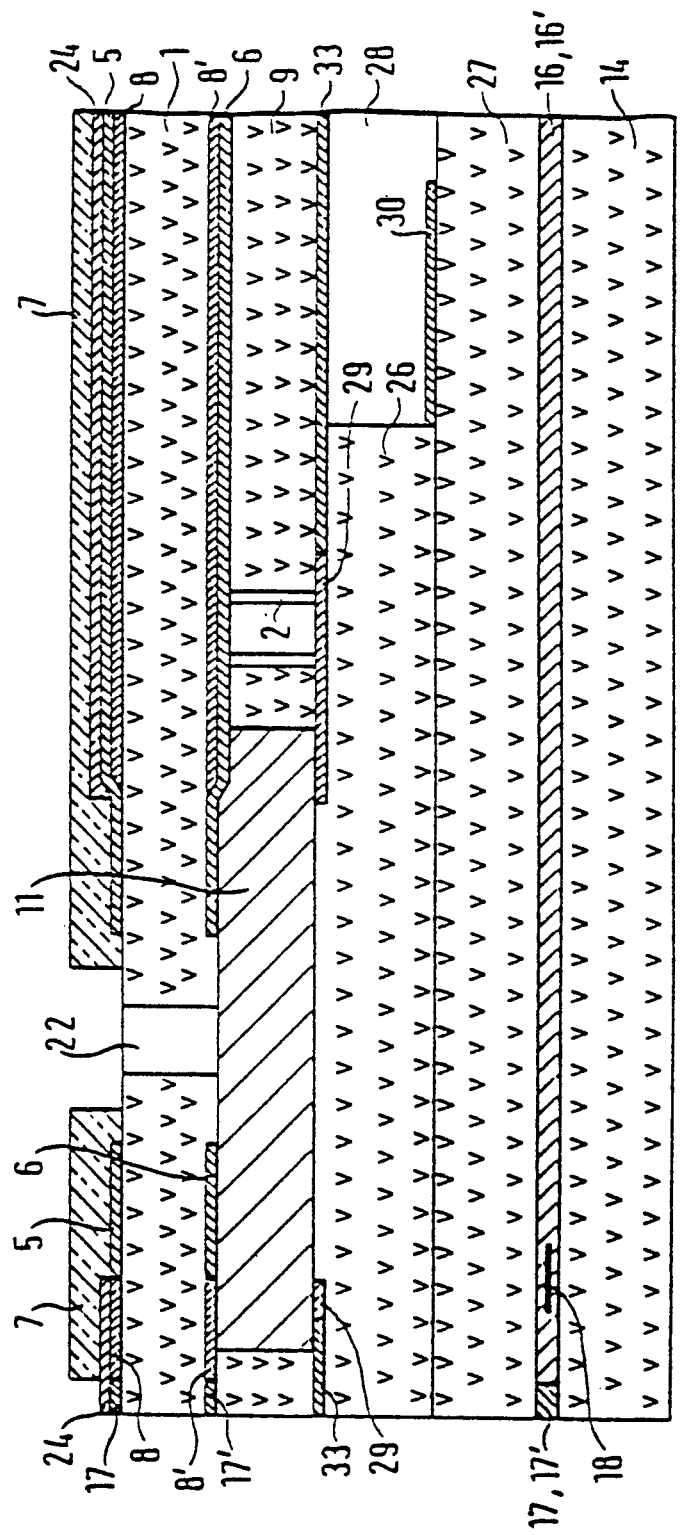
FIG. 15 shows a longitudinal section through the diffusion zone of a wideband sensor according to FIG. 13.

In contrast to the embodiments of polarographic probes according to the invention, shown diagrammatically in FIGS. 1 to 12, the eighth embodiment of a polarographic probe according to the invention, shown diagrammatically in FIGS. 13 to 15, is a polarographic probe which has been developed into a wideband sensor and which essentially differs from the previously described polarographic probes by the fact that it exhibits a Nernst cell (N) in addition to the pumping cell (A), to the diffusion unit (B) and to the heater unit (C).

The pumping cell (A) consists of the solid electrolyte foil 1 with stamped-out diffusion hole 22 and stamped-out through-contact hole 2, the outer pumping electrode 5 with a trimming resistor, the inner pumping electrode 6, the insulations 8 and 8', frames 17 and 17', the sealing layer 24 of interlaminar binder and the porous protection layer (Engobe) 7 based on $Al_2O_3/ZrO_2$.

The diffusion unit (B) consists of the solid electrolyte foil 9 with stamped-out diffusion zone 10 and stamped-out through-contact hole 2, the layers 12 and 13 of the interlaminar binder, the porous preshaped bodies 11 and the electrically conductive connecting pin 25 of Pt paste to the inner pumping electrode 6.

The Nernst cell (N) is formed of the solid electrolyte foil 26 with stamped-out reference air channel 28 and printed-on measuring electrode (Nernst cell) 29, the solid electrolyte foil 27 with through-contact hole 2, the reference electrode 30 and the layers 31, 32 and 33 of a conventional interlaminar binder.

The heater unit (C) is constructed of the solid electrolyte foil 14 with through-contact holes 2, the heater 18, the insulations 16, 16' and 19', frames 17, 17', connections 20 for the heater 18 and the reference electrode 30, the layer 34 of conventional interlaminar binder and the electrically conductive connecting pin 35 of Pt paste to the reference electrode 30.

EXAMPLE

The production of a polarographic probe according to the invention shall be described in greater detail with the example of the probe shown diagrammatically in FIGS. 1 and 2.

To produce the pumping cell (A), a solid electrolyte foil 1 of $ZrO_2$ stabilized with $Y_2O_3$, which has a thickness of about 0.3 mm in the unsintered state, was insulated by applying $Al_2O_3$—layers 4 and 8 with a thickness of about 15 to 20 $\mu m$ to both sides of the solid electrolyte foil 1.

After that, a through-contact hole 2 for the conductor track connection of the inner pumping electrode 6 was stamped out. After producing the through-contact, the outer and the inner pumping electrode 5 and 6 and associated conductor tracks were printed on, using a conventional Pt cermet paste. The through-contact hole 2 was provided with an electrically conductive $Pt/Al_2O_3$ cermet layer for the purpose of the through contact. A layer 8 of a conventional interlaminar binder of YSZ binder compound was then printed onto the side of the solid electrolyte foil 1 exhibiting the inner pumping electrode 6.

To produce the diffusion unit (B), a second solid electrolyte foil 9 of $ZrO_2$ stabilized with $Y_2O_3$ with a thickness of about 0.3 mm in the unsintered state was printed on both sides with binder layers 12 and 13 of YSZ binder compound whereupon a circular diffusion zone 10 with a diameter of 3.85 mm was stamped out.

From a further solid electrolyte foil based on $Y_2O_3$-stabilized $ZrO_2$ with a porosity of 20–30%, which becomes porous on sintering and has a thickness of 0.3 mm, a circular preshaped body 11 of a diameter of 3.8 mm was stamped out and inserted into the diffusion zone 10 of the solid electrolyte foil 9 forming the diffusion unit (B).

To produce the heater unit (C), $Al_2O_3$-based insulations 16 and 19, for insulating the heater 18 and the heater connections 20 and a frame 17 of interlaminar binder were printed onto a third solid electrolyte foil 14 of $Y_2O_3$-stabilized $ZrO_2$ with a thickness of 0.3 mm in the unsintered state. After that, the through-contact holes 15 were stamped out. The through-contact holes 15 were provided with an $Al_2O_3$ insulation layer and over that with an electrically conductive $Pt/Al_2O_3$ cermet layer. After that, the heater 18, using a $Pt/Al_2O_3$ cermet paste, an $Al_2O_3$ insulation layer 19 and a frame 17' of interlaminar binder of YSZ binder compound were printed on. After that, a layer 21 of an interlaminar binder was applied to the insulation layer 19. Finally, the diffusion hole 22 was stamped or drilled.

After the three units (A), (B) and (C) were laminated together, the compound body obtained was sintered at a temperature in the range of 1400° C.

The polarographic probe produced was inserted into a housing of the type known from German Offenlegungsschrift 3,206,903 and used for determining the $\lambda$ value of gas mixtures. Excellently reproducible results were obtained.

A polarographic probe according to the invention is preferably produced by machine in multiple image mode. The width of the probe is advantageously about 4 to 6 mm. In this connection, the electrode diameter is advantageously 3 to 4 mm, for example 3.6 mm.

We claim:

1. Planar polarographic probe for determining the lambda value of gas mixtures, particularly of exhaust gases of internal combustion engines, having at least the following units:
   a pumping cell (A),
   a diffusion unit (B) with a diffusion resistance preceding a pumping electrode (6) of the pumping cell (A) and
   a heater unit (C),
made of at least three solid electrolyte foils, namely,
   a first solid electrolyte foil (1) forming the pumping cell (A) and having an outer and an inner pumping electrode (6),
of which the inner pumping electrode is arranged
on the solid electrolyte foil (1)
in a diffusion zone (10) for the gas being measured
and
conductive tracks for the pump electrodes;
a second solid electrolyte foil (9) having a diffusion
zone and forming the diffusion unit (B); and
a third solid electrolyte foil (14) forming heater unit
(C);
the diffusion zone (10) being defined exclusively by
an aperture, formed near the inner pumping electrode, in the second solid electrolyte foil (9) laminated together with the first solid electrolyte foil
(1) and the third solid electrolyte foil (14),
and
a porous sintered body (11) filling said aperture,
made by the steps of sintering a ceramic foil to render
the same porous, and
embedding the resulting porous sintered body (11) in
said aperture, thereby protecting said body against
damage during any subsequent lamination step.

2. Polarographic probe according to claim 1, characterized in that it is constructed of at least three solid electrolyte foils, namely a first solid electrolyte foil which forms the pumping cell (A) and exhibits an outer and an inner pumping electrode, the inner pumping electrode of which is arranged on the solid electrolyte foil in a diffusion zone for the gas to be measured, and conductor tracks for the pumping electrodes, a second solid electrolyte foil which forms the diffusion unit (B) and exhibits a diffusion zone, and a third solid electrolyte foil which is constructed to form a heater unit (C), and in that the diffusion zone (10) is formed by a recess in the second solid electrolyte foil (9), which is laminated together with the first solid electrolyte foil (1) and the third solid electrolyte foil (14), in the area of the inner pumping electrode (5), into which a preshaped body (11) is inserted which becomes porous on sintering during the sintering process of the probe.

3. Polarographic probe according to claim 2, characterized in that the third solid electrolyte foil (14) which is constructed to form a heater unit (C) and/or the first solid electrolyte foil which is constructed to form a pumping cell (A) exhibits a diffusion hole (22) for the admission of the gas to be measured into the diffusion zone (10).

4. Polarographic probe according to one of claim 1 characterized in that the preshaped bodies (11) in the diffusion zone (10) consists of a porously sintered ceramic material.

5. Polarographic probe according to claim 4, characterized in that the preshaped bodies (11) consists of a porously sintered ceramic material which at least predominantly is formed of $ZrO_2$ and/or $Al_2O_3$.

6. Polarographic probe according to one of claim 4 characterized in that the preshaped bodies (11) fully fills out the diffusion zone (10) in the second solid electrolyte foil (9).

7. Polarographic probe according to one of claim 1 characterized in that an air gap is located between the inner pumping electrode (5) and the preshaped bodies (11).

8. Polarographic probe according to claim 1 characterized in that the third solid electrolyte foil (14), which is constructed to form a heater unit (C), exhibits a diffusion hole (22) for the entry of the gas to be measured into the diffusion zone (10) and in that the preshaped bodies (11) consists of a lamina exhibiting a central hole.

9. Polarographic probe according to claim 1 characterized in that the mean pore diameter of the porously sintered preshaped bodies (11) is 5 to 50 μm.

10. Polarographic probe according to claim 2 characterized in that the solid electrolyte foils forming the structure of the probe consist of $Y_2O_3$-stabilized $ZrO_2$.

11. Planar polarographic probe for determining the lambda value of gas mixtures, particularly of exhaust gases of internal combustion engines, comprising
a pumping cell (A),
a diffusion unit (B) with a diffusion resistance preceding a pumping electrode (6) of the pumping cell (A) and
a heater unit (C),
made of at least three solid electrolyte foils, namely,
a first solid electrolyte foil(1) forming the pumping cell (A) and having
an outer and an inner pumping electrode (6),
of which the inner pumping electrode is arranged on the solid electrolyte foil (1)
in a diffusion zone (10) for the gas being measured and
conductive tracks for the pump electrodes;
a second solid electrolyte foil (9) having a diffusion zone and forming the diffusion unit (B); and
a third solid electrolyte foil (14) forming said heater unit (C);
the diffusion zone (10) being defined exclusively by an aperture, formed near the inner pumping electrode, in the second solid electrolyte foil (9) laminated together with the first solid electrolyte foil (1) and the third solid electrolyte foil (14), into which aperture a porous sintered body (11), formed during a probe sintering process, is embedded;
and further comprising a Nernst cell (N) having first and second electrodes,
said first electrode being exposed to exhaust gas by being located adjacent the pumping electrode behind the preshaped bodies (11) which becomes porous on sintering and forms the diffusion resistance,
said second electrode being exposed to a reference medium.

* * * * *